United States Patent
Minamiura et al.

(10) Patent No.: US 7,052,469 B2
(45) Date of Patent: May 30, 2006

(54) HEART BEAT/RESPIRATION MEASURING DEVICE

(75) Inventors: Takeshi Minamiura, Moriguchi (JP); Hidetaka Sakai, Moriguchi (JP); Akira Sakaguchi, Moriguchi (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 106 days.

(21) Appl. No.: 10/707,070

(22) Filed: Nov. 19, 2003

(65) Prior Publication Data

US 2004/0111039 A1    Jun. 10, 2004

(30) Foreign Application Priority Data

Nov. 25, 2002    (JP) .............................. 2002-340311

(51) Int. Cl.
*A61B 5/00* (2006.01)
(52) U.S. Cl. ....................... 600/534; 600/529
(58) Field of Classification Search ........ 600/529–538, 600/481–503
See application file for complete search history.

(56) References Cited

U.S. PATENT DOCUMENTS

| | | | |
|---|---|---|---|
| 4,648,407 A * | 3/1987 | Sackner ....................... | 600/534 |
| 5,301,678 A * | 4/1994 | Watson et al. ................ | 600/534 |
| 6,142,953 A * | 11/2000 | Burton et al. ................. | 600/534 |
| 2004/0103475 A1 * | 6/2004 | Ogawa et al. ................. | 5/613 |

FOREIGN PATENT DOCUMENTS

| | | |
|---|---|---|
| GB | 1 596 298 | 8/1981 |
| JP | 53-126789 | 11/1978 |
| JP | 2-48252 | 10/1990 |
| JP | 4-33641 | 2/1992 |
| JP | 5-65176 | 9/1993 |

OTHER PUBLICATIONS

T. Ohkubo et al.; "A System for Measuring Movements of a Patient Using Capacitance-Type Sensors"; *Medical Electronics and Biomedical Engineering*; vol. 32-2; No. 132-135; pp. 50-53; 1994/Partial translation/Discussed in the specficiation.

T. Minamiura et al.; "Development of Portable Non-Restrictive Sleep Sensor"; *The 2002 Institute of Electronics Information and Communication Engineers General Conference Abstract*; No. D-7-25; p. 94/Discussed in the specification.

* cited by examiner

*Primary Examiner*—Robert L. Nasser
(74) *Attorney, Agent, or Firm*—Armstrong, Kratz, Quintos, Hanson & Brooks, LLP

(57) ABSTRACT

A heart beat/respiration measuring device comprising a sensor adapted to be pressed against the human body, and a measuring circuit for measuring heart beats and respiration from the output of the sensor. The sensor includes a coil member elastically deformable when subjected to pressure by being pressed against the human body. The measuring circuit comprises an LC oscillation circuit wherein an inductance component and a capacitance component of the coil member serve respectively as a coil L and a capacitor C for oscillation, and a calculation processing circuit for detecting variations in the oscillation frequency of the LC oscillation circuit and calculations of a cardiac cycle, heart rate, respiratory cycle and respiration rate based on the frequency components of heart beats and respiration are included in the variations.

3 Claims, 7 Drawing Sheets

HEART BEAT/RESPIRATION MEASURING DEVICE

FIELD OF THE INVENTION

The present invention relates to heart beat/respiration measuring devices for measuring the heart beats and/or respiration of the human body.

BACKGROUND OF THE INVENTION

1. Field of the Invention

With the aging of society in recent years, there is an increase in the number of bedridden persons, and attention has been directed to the method of conducting diagnosis based on variations in the heart rate as measured by an electrocardiograph as a method of monitoring the physical condition of the bedridden elderly person. Presently, with growing awareness of health management, people have become more desirous of readily measuring the heart rate during sleep in the ordinary family.

2. Description of the Related Art

However, when the conventional electrocardiograph is to be used for measuring the heart rate, there is a need to affix a plurality of electrodes directly to the skin, and the conventional device therefore has the drawback that the person to be checked is held restrained for a prolonged period of time by the cords extending from the electrodes to the main body of the instrument. Because of the same situation involved in measuring the respiration rate, difficulty is encountered in making the measurement easily in the home.

Accordingly, systems are known for measuring the dynamic conditions of patients using a capacitance-type sensor [(i) Tomohiro Ohkubo and Yoshimichi Yonezawa, "System for Measuring Dynamic Conditions of Patients by Capacitance-Type Sensor," Medical Electronics and Biomedical Engineering, 32-2, 132/135, 1994, (ii) Takeshi Minamiura, Yoshihisa Fujiwara, Hidetaka Sakai, Hidefumi Matsuura and Shoji Yasuda, "Development of Portable Nonrestraint Sleep Sensor," Society of Electronics, Information and Communications, 2002 General Meeting, Abstracts, D-7-25).

Although the heart rate or respiration rate of patients can be measured by such a sensor free of restraint, the sensor still remains to be improved with respect to the sensitivity of measurement.

SUMMARY OF THE INVENTION

An object of the present invention is to provide a heart rate/respiration measuring device which is adapted to measure the heart beats or respiration of the human body free of restraint and with high sensitivity.

The present invention provides a heart beat/respiration measuring device comprising a sensor 2 to be pressed against the human body, and a measuring circuit for measuring heart beats and/or respiration from the output of the sensor 2. The sensor 2 comprises a coil member elastically restorably deformable when subjected to pressure by being pressed against the human body, the measuring circuit comprising an LC oscillation circuit 3 wherein an inductance component and a capacitance component of the coil member serve respectively as a coil L and a capacitor C for oscillation, and a calculation processing circuit 4 for detecting variations in the oscillation frequency of the LC oscillation circuit 3 and calculating physiological data in accordance with heart beats and/or respiration based on the frequency component or components of heart beats and/or respiration included in the variations. For example, the coil member of the sensor 2 can be made by winding a wire around an elastic member.

With the heart beat/respiration measuring device of the present invention, the sensor 2 is installed under the human body lying face up, face down or on one side thereof. Accordingly, the sensor 2 is subjected to pressure by being pressed against the human body with the heart beats and respiration of the body. As a result, the sensor 2 elastically deforms.

The sensor 2 can be installed in a posture in which the pressure acts in a direction orthogonal to the winding axis of the coil member. In this case, the sensor 2 is compressed in the direction orthogonal to the winding axis of the coil member by being subjected to the pressure, and is altered in cross sectional area. Alternatively, the sensor 2 can be installed in a posture in which the pressure acts in a direction along a winding axis of the coil member. In this case, the sensor 2 is compressed in the direction along the winding axis of the coil member by being subjected to the pressure, and is altered in length.

The coil member which is spiral and constitutes the sensor 2 has an inductive component and a capacitive component. The inductance varies with the variation of the cross sectional area or length, and the capacitance varies due to the elastic deformation of the sensor 2, variations in the distance between the turns of wire of the coil and variations in the distance between the coil and the human body. The variations in the inductance and capacitance include frequency components of heart beats and respiration.

The LC oscillation circuit 3 varies in oscillation frequency with variations in the inductance and capacitance of the sensor 2. The calculation processing circuit 4 detects the variations in oscillation frequency, and calculates physiological data (e.g., heart rate, respiration rate, cardiac cycle or respiratory cycle) in accordance with heart beats and/or respiration, from the frequency component or components of heart beats and/or respiration included in the variations.

The heart beat/respiration measuring device of the invention is usable with the sensor installed, for example, in a bed or mat, so that the heart beats or respiration of the human body can be measured free of restraint. The heart beat or respiration measurement can be obtained with high accuracy because both the inductance and capacitance of the sensor vary with the heart beats or respiration.

DETAILED DESCRIPTION OF THE PREFERRED EMBODIMENT

Figure 1:
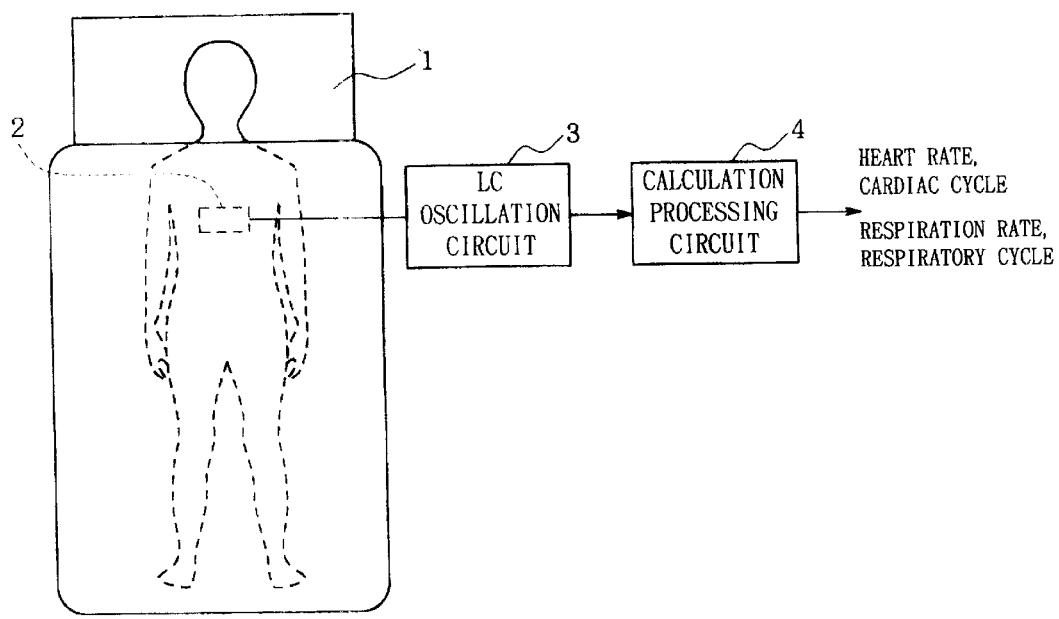
FIG. 1 is a block diagram showing the construction of a heart beat/respiration measuring device embodying the present invention.
Figure 2:
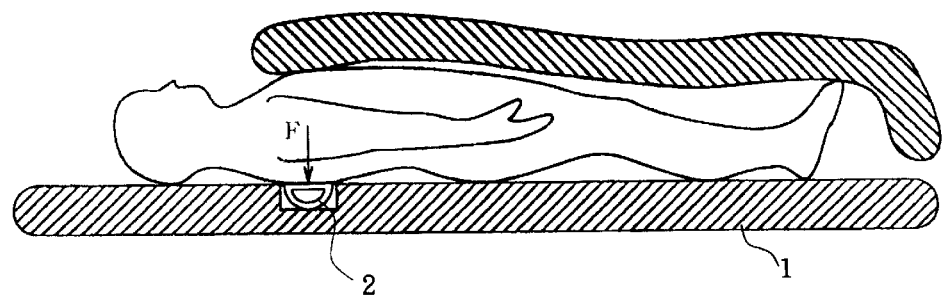
FIG. 2 is a diagram for illustrating the position where a sensor is to be installed.

A preferred embodiment of the invention will be described below in detail with reference to the drawings. The heart beat/respiration measuring device of the invention comprises a sensor 2 disposed on the surface of a mat 1 for the upper half of the human body as shown in FIGS. 1 and 2. The sensor 2 is subjected to pressure by being pressed against the upper half of the human body.

Figure 3:
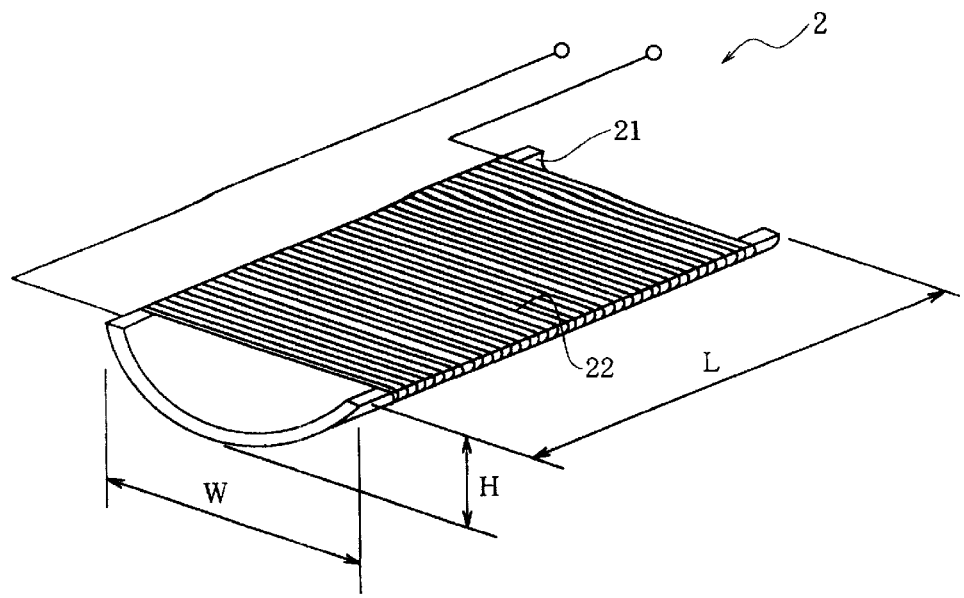
FIG. 3 is a perspective view showing the construction of the sensor.

With reference to FIG. 3, the sensor 2 comprises an elastic member 21 in the form of a resin plate curved in a circular-arc form, and a coil 22 wound around the elastic member 21. The elastic member 21 is rectangular in shape when seen from above, in the form of a laterally elongated semiellipse in cross section and measures 250 mm in length L along the direction of the winding axis, 150 mm in width W in a direction orthogonal to the winding axis and 9 mm in height H. The coil 22 is formed by winding a soft copper wire of 0.2 mm in diameter around the elastic member 21 about 450 turns.

The elastic member 21 thus inserted into the inside space of the coil 22 of the sensor 2 prevents the coil 22 from collapsing and ensures the elastic restoration of the coil 22. In place of the elastic resin member 21, a sponge, air bag, spring or the like can be inserted into the inside space of the coil 22. Improved measuring accuracy can be achieved also by providing an elastic resin member, sponge, air bag, spring or the like in an external space around the coil 22.

Figure 4:
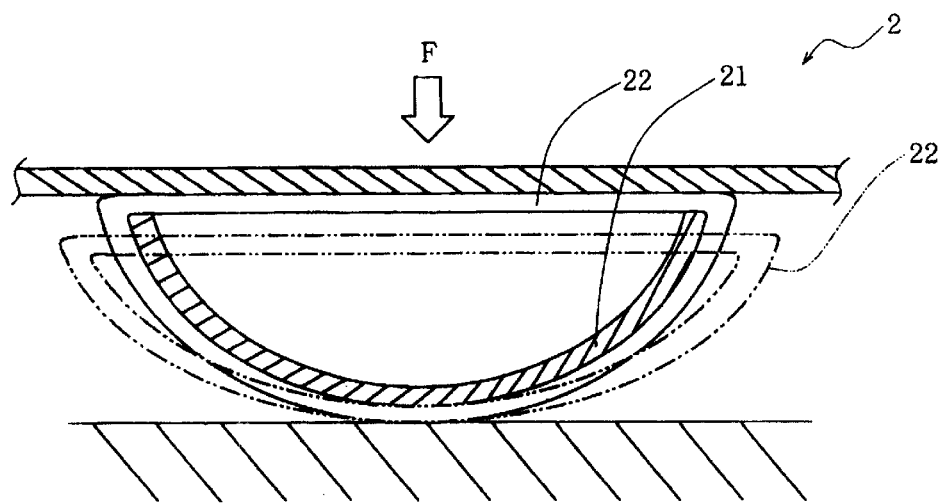
FIG. 4 is a diagram showing how the sensor is elastically deformed.

The sensor 2 is subjected to pressure F with the heart beats or respiration of the human body by being pressed by the upper half of the human body lying face up, face down or on one side thereof as shown in FIGS. 1 and 2. The sensor 2 is elastically deformed as indicated in chain lines in FIG. 4 from an unloaded state indicated in solid lines in the drawing, altered in cross sectional area with variations in the pressure and also altered in the distance between the turns of wire of the coil 22 and the distance of the coil 22 from the human body.

Suppose the sensor 2 has an inductance L, magnetic permeability $\mu_0$ in a vacuum, a cross sectional area A, and is N in the number of turns of the coil, L in length and K in Nagaoka coefficient. The sensor 2 then has the relationship of Mathematical Expression 1 given below.

(Mathematical Expression)

$$L = K(\mu_0 A N^2 / L)$$

Accordingly, variations in the cross sectional area A of the sensor 2 vary the inductance L of the sensor 2. The variation of the inductance includes frequency components of heart beats and respiration.

The coil member constituting the sensor 2 has not only an inductance component but also a capacitance component, so that capacitance C is also altered by the elastic deformation of the sensor 2 due to the pressure exerted by the human body, variations in the distance between the turns of wire of the coil 22 and the variations in the distance between the coil 22 and the human body. The alteration of the capacitance includes frequency components of heart beats and respiration.

As shown in FIG. 1, the sensor 2 has connected thereto an LC oscillation circuit 3 wherein the sensor 2 serves as oscillation coil and capacitor. Further connected to the LC oscillation circuit 3 is a calculation processing circuit 4 comprising a microcomputer, etc.

Figure 5:
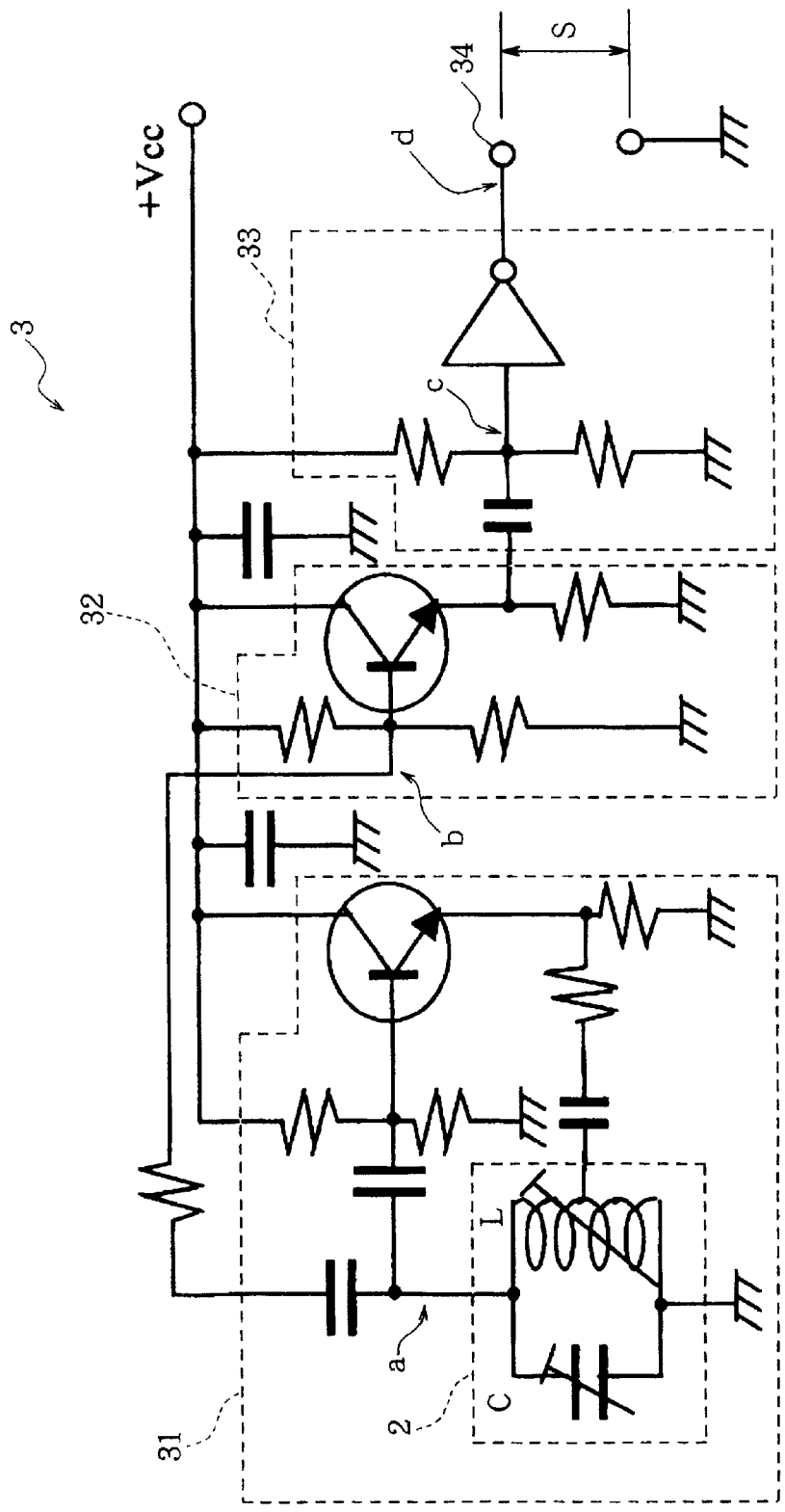
FIG. 5 is a circuit diagram showing an exemplary construction of an LC oscillation circuit.

With reference to FIG. 5, the sensor 2 can be represented by an equivalent circuit comprising a coil L and a capacitor C which are connected in parallel. The LC oscillation circuit 3 comprises an LC oscillation circuit portion 31 including the sensor 2, a buffer circuit portion 32 for feeding an oscillation signal to an output stage without interfering with the operation of the LC oscillation circuit portion 31, and a shaping circuit portion 33 for converting the oscillation signal obtained by the buffer circuit portion 32 and comprising a sine wave to an oscillation signal of rectangular wave. The shaping circuit portion 33 is connected to an output terminal 34.

The oscillation frequency $f_0$ of the LC oscillation circuit 3 is expressed by Mathematical Expression 2 given below.

(Mathematical Expression 2)

$$f_0 = 1/(2\pi \cdot \sqrt{(LC)})$$

Figure 7:
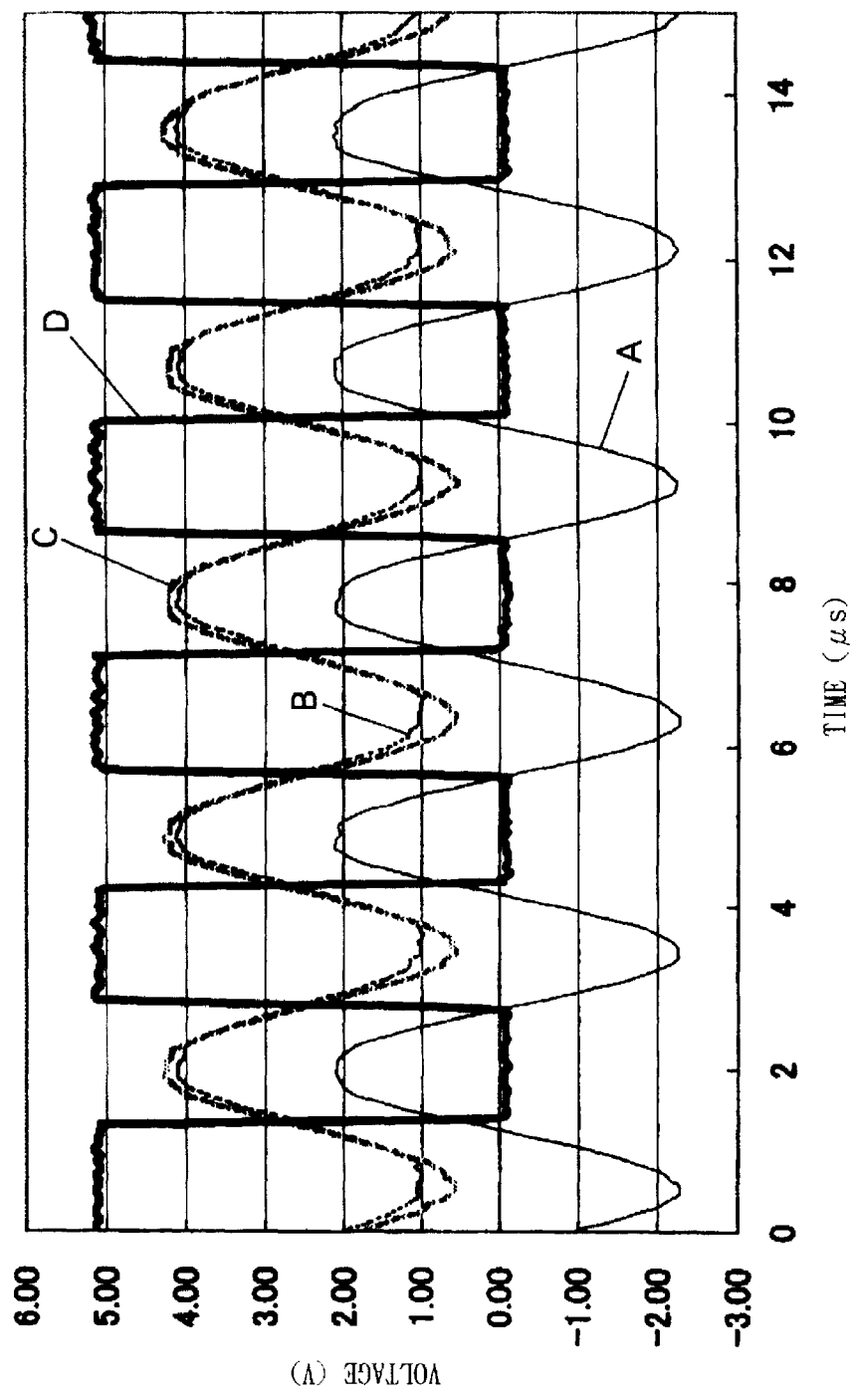
FIG. 7 is a graph showing waveforms at different points of the LC oscillation circuit.

FIG. 7 shows voltage waveforms at different points of the LC oscillation circuit 3. Indicated at A is a voltage waveform at the output end a of the sensor 2, at B a voltage waveform at the input end b of the buffer circuit portion 32, at C a voltage waveform at the input end c of the shaping circuit portion 33, and at D a voltage waveform at the output end d of the shaping circuit portion 33.

Figure 6:
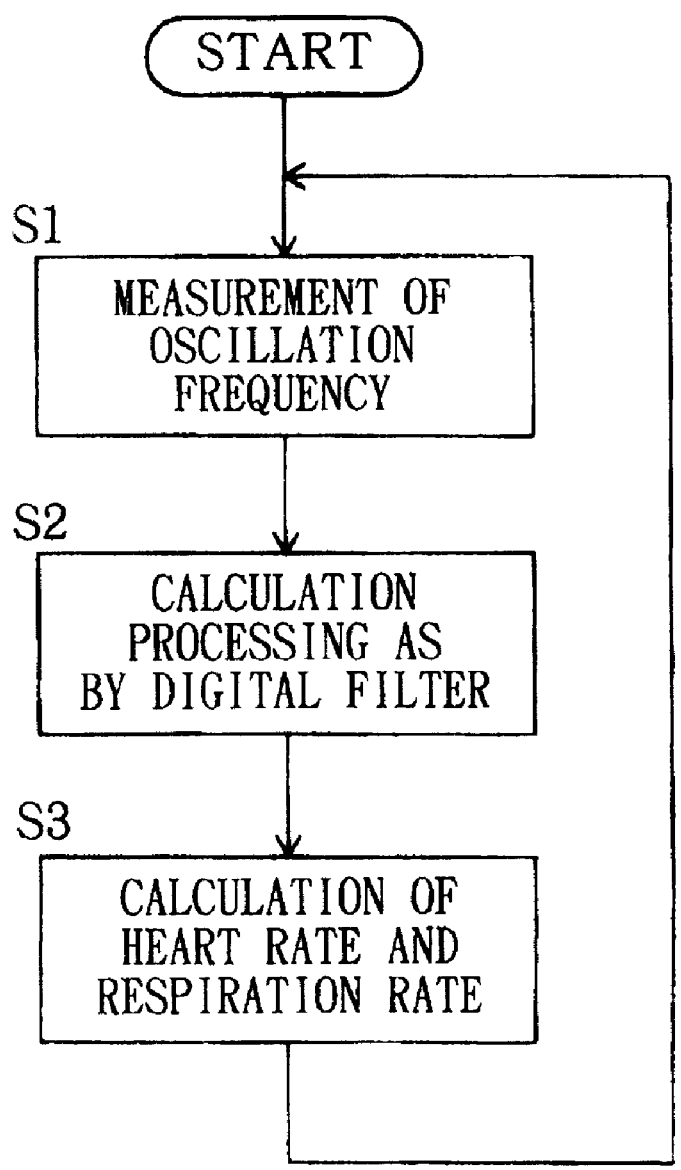
FIG. 6 is a flow chart for illustrating the operation of a calculation processing circuit.

The LC oscillation circuit 3 produces a voltage signal of rectangular waveform, which is fed to the calculation processing circuit 4 as shown in FIG. 1. With reference to FIG. 6, the calculation processing circuit 4 first measures an oscillation frequency in step S1 by counting the number of pulses of the voltage signal of rectangular waveform per unit time by a counter incorporated in the circuit. Variations in the oscillation frequency include the frequency component of heart beats and the frequency component of respiration.

The variation of oscillation frequency measured is subjected to calculation processing as by a digital filter subsequently in step S2 to extract the frequency component of heart beats and the frequency component of respiration. The heart rate and the respiratory rate are calculated from the extracted frequency component of heart beats and frequency component of respiration finally in step S3.

Figure 8:
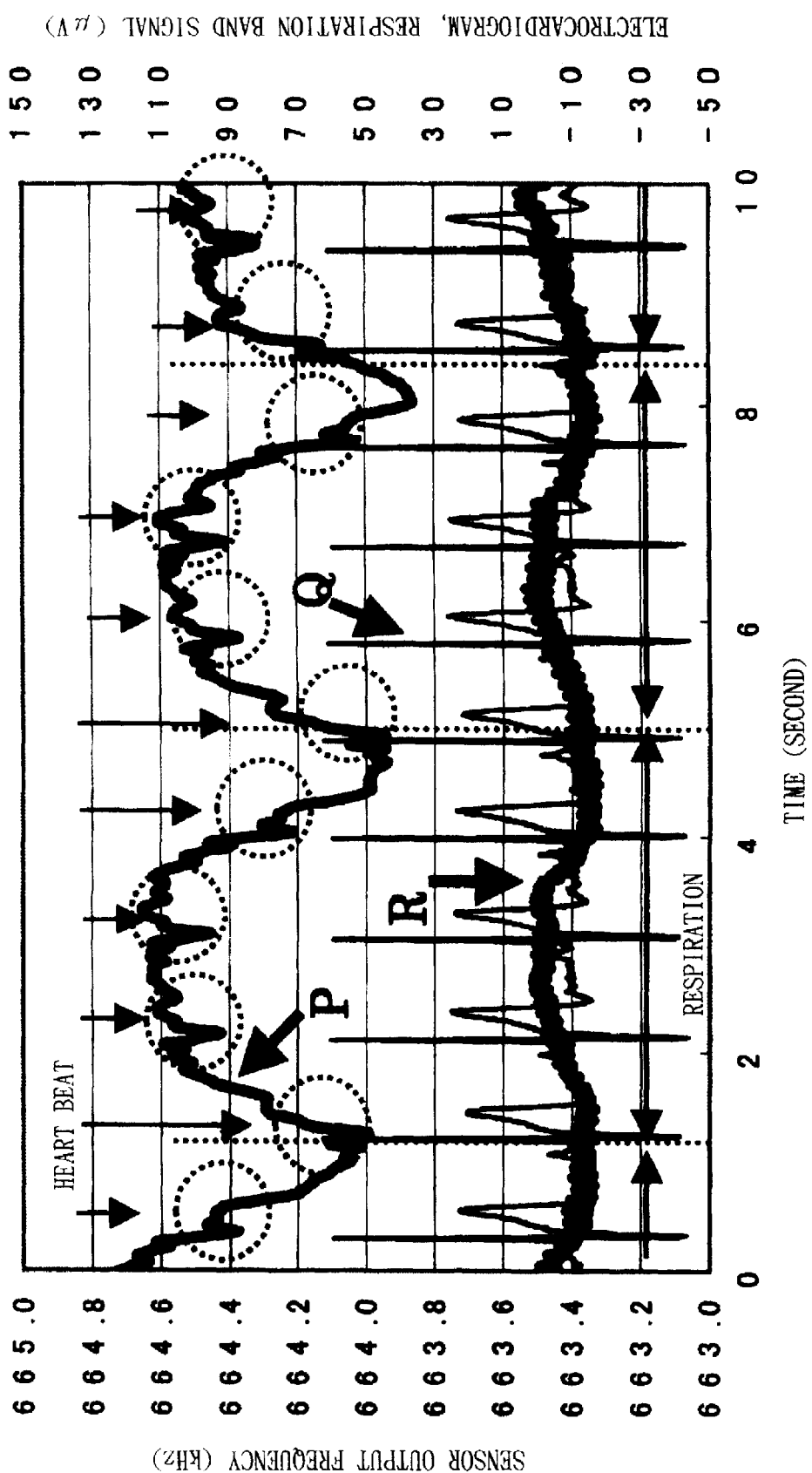
FIG. 8 is a graph showing variations in oscillation frequency as measured by the heart beat/respiration measuring device of the invention, an electrocardiogram as recorded by an electrocardiograph and voltage variations due to respiration and as measured by a respiration measuring instrument.

FIG. 8 shows variations P in the oscillation frequency as measured by the calculating circuit 4, an electrocardiogram Q as recorded by an electrocardiograph (not shown) and voltage variations R due to respiration and as measured by a respiration measuring instrument (not shown). As illustrated, the variations P in the oscillation frequency apparently include the frequency component of heart beats and that of respiration.

Figure 9:
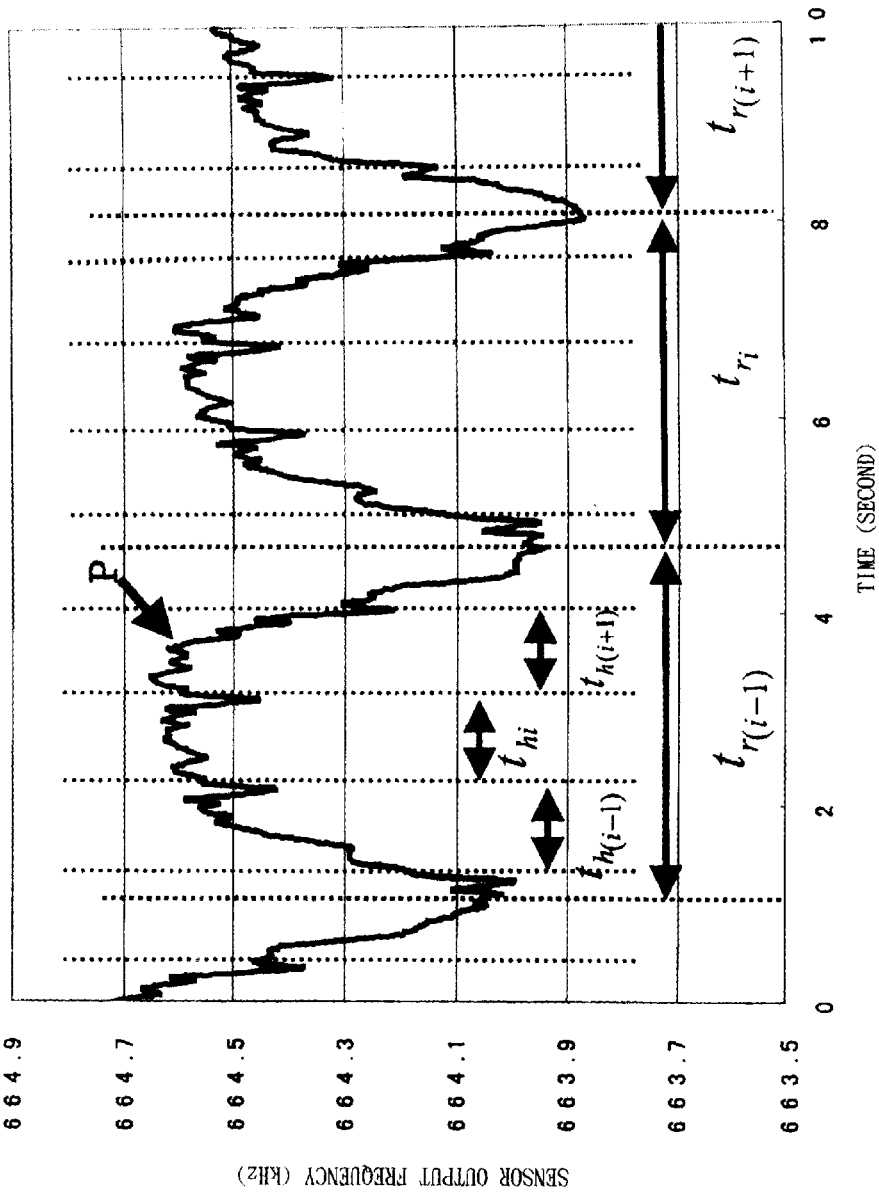
FIG. 9 is a graph showing the variations in oscillation frequency mentioned.

FIG. 9 shows on an enlarged scale some of the variations P in the oscillation frequency shown in FIG. 8. The cardiac cycle and the respiratory cycle can be detected by measuring the period of time from the beginning of one beat of the heart to the beginning of the succeeding beat and the period of time from the beginning of one respiration to the beginning of the succeeding respiration, respectively, based on the variations P in the oscillation frequency as illustrated. FIG. 9 shows that the cardiac cycle is $t_{hi}$ (sec), and that the respiratory cycle is $t_{ri}$ (sec). These results lead to a heart rate per minute of $60/t_{hi}$, and a respiration rate of $60/t_{ri}$.

Thus, the calculation processing of the variations in the oscillation frequency as by the filter processing extracts the frequency component of heart beats and the frequency component of respiration from the variations, consequently giving the cardiac cycle, heart rate, respiratory cycle and respiration rate.

In the case of the heart beat/respiration measuring device of the invention, the sensor 2 can be attached to the mat 1, so that the heart rate and respiration rate of the human body in a recumbent position can be measured without restraining the human body. With the device of the invention, both the inductance and capacitance of the sensor vary with heart beats and respiration, with the result that the heart rate and respiration rate can be calculated with high accuracy.

The device of the present invention is not limited to the foregoing embodiment in construction but can be modified variously within the technical scope defined in the appended claims. For example, the coil member constituting the sensor 2 is not limited to the above embodiment with respect to the dimensions and the number of turns of the wire.

The coil member constituting the sensor 2 need not always be made elastically deformable diametrically thereof as installed in a posture in which the pressure acts thereon in a direction orthogonal to the winding axis. Alternatively, the coil member can be installed in such a position that the pressure will act in the direction of the winding axis so as to elastically deform in the direction of the winding axis. In this case, a spring incorporated in a bed can be utilized as the coil member of the sensor 2.

The embodiment described is adapted to measure the oscillation frequency by counting the number of pulses per unit time of the voltage signal having a rectangular waveform and delivered from the LC oscillation circuit 3, and to extract the frequency component of heart beats and the frequency component of respiration from the oscillation frequency, whereas this method is not limitative; it is possible to convert oscillation frequency measurements to voltage values and to detect variations in the oscillation frequency based on the voltage values.

Usable as a method of detecting variations in oscillation frequency based on voltage values is a method wherein variations in oscillation frequency are output as voltage values using a known PLL. In this case, the voltage signal of rectangular waveform obtained at the output end d shown in FIG. 5 is given to the PLL as a reference frequency, which is compared with the output frequency in phase to alter the voltage to be applied to a VCO circuit so as to match the frequencies in phase. The voltage to be applied to the VCO circuit is measured, whereby variations in the pulse frequency of the voltage signal of rectangular waveform obtained at the output end d can be measured as voltage variations.

What is claimed is:

1. A heart beat/respiration measuring device comprising:
   a mat;
   a sensor (2) disposed in a recess in said mat and adapted to be pressed against a human body as the human body lies on said mat; and
   a measuring circuit for measuring heart beats and/or respiration from the output of the sensor (2),
   the sensor (2) comprising a coil member comprising a wire wound around an elastic member having a hollow portion and being elastically restorably deformable with subjected to pressure by being pressed against the human body, and
   the measuring circuit comprising an LC oscillation circuit (3) wherein an inductance component and a capacitance component of the coil member serve respectively as a coil L and a capacitor C for oscillation, and a calculation processing circuit (4) for detecting variations in the oscillation frequency of the LC oscillation circuit (3) and calculating physiological data in accordance with heart beats and/or respiration based on the frequency component or components of heart beats and/or respiration included in the variations.

2. A heart beat/respiration measuring device according to claim 1, wherein the sensor (2) is installed in a posture in which the pressure acts in a direction orthogonal to a winding axis of the coil member.

3. A heart beat/respiration measuring device according to claim 1, wherein the sensor (2) is installed in a posture in which the pressure acts in a direction along a winding axis of the coil member.

* * * * *

UNITED STATES PATENT AND TRADEMARK OFFICE
CERTIFICATE OF CORRECTION

PATENT NO. : 7,052,469 B2 Page 1 of 1
APPLICATION NO. : 10/707070
DATED : May 30, 2006
INVENTOR(S) : Takeshi Minamiura et al.

It is certified that error appears in the above-identified patent and that said Letters Patent is hereby corrected as shown below:

In Claim 1:
Column 6, Line 20, change "with subjected" to be -- when subjected --

Signed and Sealed this

Third Day of October, 2006

JON W. DUDAS
*Director of the United States Patent and Trademark Office*